(12) United States Patent
Chen et al.

(10) Patent No.: US 8,568,440 B2
(45) Date of Patent: Oct. 29, 2013

(54) ESTIMATION OF PRESSURE AT REMOTE SITE BY BRACHIAL OSCILLOMETRIC WAVEFORM ANALYSIS

(75) Inventors: Chen-Huan Chen, Taipei (TW); Hao-Mim Cheng, Taipei (TW)

(73) Assignee: National Yang-Ming University, Taipei (TW)

( * ) Notice: Subject to any disclaimer, the term of this patent is extended or adjusted under 35 U.S.C. 154(b) by 1156 days.

(21) Appl. No.: 12/132,826

(22) Filed: Jun. 4, 2008

(65) Prior Publication Data
US 2009/0149763 A1   Jun. 11, 2009

(30) Foreign Application Priority Data
Dec. 10, 2007 (TW) .............................. 96147043 A

(51) Int. Cl.
*A61B 17/12* (2006.01)
*A61B 5/0205* (2006.01)
*A61B 5/021* (2006.01)
*A61B 5/022* (2006.01)
*A61B 5/0295* (2006.01)

(52) U.S. Cl.
USPC ........... 606/201; 606/202; 600/481; 600/485; 600/490; 600/501; 600/504

(58) Field of Classification Search
USPC .......... 606/201, 202; 600/481, 485, 490, 493, 600/494, 495, 500, 501, 502, 504, 595
See application file for complete search history.

(56) References Cited

U.S. PATENT DOCUMENTS 5,054,494 A * 10/1991 Lazzaro et al. ............... 600/490

* cited by examiner

*Primary Examiner* — Stacy B. Chen
(74) *Attorney, Agent, or Firm* — WPAT, P.C.; Anthony King

(57) ABSTRACT

The present invention relates to a device and a method for estimating central systolic blood pressure based on oscillometric signals from brachial artery by the use of a pressure cuff.

5 Claims, 6 Drawing Sheets

Figure

ESTIMATION OF PRESSURE AT REMOTE SITE BY BRACHIAL OSCILLOMETRIC WAVEFORM ANALYSIS

FIELD OF THE INVENTION

The present invention relates to a method that dynamically analyzes the form of pressure wave in cuff recorded during measurement of blood pressure by electronic manometer. The analytic method measures the central arterial systolic blood pressure accurately, and the manometer employing the technology of the present invention can simultaneously measure the traditional peripheral arterial (brachium artery) blood pressure as well as the central arterial blood pressure. The present invention largely improves the accuracy of hypertensive medicine choice and the dosage adjustment.

BACKGROUND OF THE INVENTION

Abnormality of blood dynamics is usually occurred in hypertension, including enhancement of reflected wave, acceleration of pulse conduction and decrease of compliance. It has been clinically proven that the central arterial pressure is a key factor of recovery from hypertension. The brachium arterial blood pressure value is determined by measurement of the peripheral arterial blood pressure by traditional or electronic manometer, usually being higher than the central arterial blood pressure, such as the ascending aortic and carotid arterial blood pressure value. Due to the different effects of different medications of blood pressure-lowering medicine on the central aortic and peripheral arterial blood pressure, using the brachium arterial systolic and diastolic blood pressure measured alone by traditional or electronic manometer to estimate the central aortic blood pressure may overestimate or underestimate the effect of blood pressure-lowering medicine on the central aortic blood pressure. Hence, it is insufficient to evaluate how well the blood pressure is controlled only by measuring of the brachium arterial blood pressure. There has been a method already which can estimate the waveform and value of ascending aortic systolic blood pressure by recording the radial arterial waveform, the brachium arterial blood pressure, and by a known mathematic formula, the related commercialized product (SphygmoCor, AtCor Medical Pty Limited) has been widely used in clinical trial, and it has been proven that the estimation of the value of ascending aortic systolic blood pressure can show the different effects on the central aortic blood pressure by different medications of blood pressure-lowering medicine. It could predict the risk of patients with cardiovascular disease after medication of different pressure-lowering medicines; hence, the measurement of the central arterial blood pressure played a role in the control of hypertension. Although SphygmoCor can estimate the ascending aortic systolic blood pressure, it needs expensive and complicated accessories and special operation techniques and is not appropriate for widely use in hospital and personal use of a patient.

Patent No. WO/1996/0390 showed an innovation of technology, employing two separated measurement parts (upper arm and wrist) to measure the brachium arterial blood pressure value (by technology of common electronic manometer) and the radial arterial blood pressure waveform (by pen-shaped arterial tonometer) respectively, and then converts the radial arterial blood pressure waveform to the ascending aortic blood pressure waveform by a known mathematic formula, and adjusts the converted ascending aortic blood pressure waveform by the measured brachium arterial blood pressure value. Users can obtain the ascending aortic blood pressure value through the converted ascending aortic blood pressure waveform, which is the commercialized, non-invasive and patented technology of estimating the waveform and value of ascending aortic blood pressure. The product of this patent, invented by an Australian scientist, Dr. Michael F. O'Rourke, needs the expensive pen-shaped pressure tonometer, a laptop, and a specialized analytic program. The pen-shaped pressure tonometer is related to the accuracy of the estimated value and needs special operation technique; therefore, the usage of the expensive diagnostic instrument is still limited to research and can not be a personal home care.

SUMMARY OF THE INVENTION

The present invention provides a measuring device of estimating the central arterial blood pressure at remote site (10), which includes:
(1) a controlling device (20) of the pressure change in the cuff, which is used to control the process of pressurization, decompression or maintenance a certain pressure value;
(2) a recording and saving device (30) of oscillometric signals of the pressure in the cuff; and
(3) an analytic device (40) of analyzing the oscillometric signals of the pressure in the cuff, which is used to estimate the central arterial blood pressure by real-time analysis of the oscillometric signals of the pressure.

The present invention further provides a method of estimating the central arterial blood pressure by measuring the signal of pulse oscillation of the brachium artery by cuff, which includes:
(1) detecting the oscillometric waveform in the cuff;
(2) adjusting the oscillometric waveform by the average blood pressure and diastolic blood pressure measured by the cuff to calculate (I) systolic blood pressure of pulse volume recording, (II) last phase systolic blood pressure of pulse volume recording, (III) the value of the area below the waveform during systole and the area below the waveform during diastole dividing the area below the waveform during diastole, and (IV) the pressure of reflected wave hiding beneath the waveform of pressure; and
(3) Bringing factors (I)~(IV) to a formula, a regression formula, to measure the measured central arterial blood pressure, and serving the measured central arterial blood pressure as a dependent variable; the factors (I)~(IV) in Step (2) as independent variable, and then to solve the formula.

DETAILED DESCRIPTION OF THE INVENTION

The present invention changes the procedure of measuring blood pressure appropriately, and uses the recorded oscillatory wave of pressure pulse in the cuff to do dynamic analysis and then estimates the central aortic systolic blood pressure accurately. The techniques of operation and analysis of the present invention can apply to a common electronic manometer without other expensive accessories. The diagnosis of hypertension can be a revolution while a common electronic manometer has the function to measure the central aortic systolic blood pressure.

The present invention relates to a method of analyzing the oscillatory wave of pressure pulse in the cuff. The present invention use the pressure value obtained from the measurement part (upper arm) to estimate the pressure value of remote parts (ascending aorta or carotid arteries) directly. In detail, the present invention is characterized by the analytic method of oscillatory waveform of pressure pulse used in the cuff of electronic manometer, including the analysis of dynamic oscillatory waveform (the oscillatory waveform recorded during decrease period of pressure in the cuff) and the analysis of static oscillatory waveform (the oscillatory waveform recorded when the pressure in the cuff decreased to certain degree, the so-called pulse volume recording). The analytic method of the present invention includes the techniques of analyzing time and frequency, which estimates the pressure value of remote parts (ascending aorta or carotid arteries) directly through real-time analysis oscillatory waveform of pressure pulse.

As Shown in FIG. 1A, the present invention employs a measurement part (cuff) as same as the one in a common electronic manometer and a special measurement device to measure the brachium arterial blood pressure value (by the technique of common pulse oscillatory electronic manometer) and record the oscillatory pressure waveform in the cuff under different pressure control (saved temporarily in dynamic memory chip) spontaneously, and then analyzes the oscillatory pressure waveform immediately by a controlling chip and estimate the central arterial (ascending aortic or carotid arterial) systolic blood pressure value. The new developed electronic manometer employed the technology of the present invention does not need any additional pressure recorder or laptop except a controlling chip and a dynamic memory chip, and the operation is as same as the one of a common electronic manometer; hence, The new developed electronic manometer can be used in hospital or personal home care.

The "central artery" refers to carotid arteries or the ascending aorta.

As shown in FIG. 1B, the present invention provides a measuring device of estimating the central arterial blood pressure at remote site (10), which includes:
(1) a controlling device (20) of the pressure change in the cuff, which is used to control the process of pressurization, decompression or maintaining a certain pressure value;
(2) a recording and saving device (30) of oscillometric signals of the pressure in the cuff; and
(3) an analytic device (40) of analyzing the oscillometric signals of the pressure in the cuff, which is used to estimate the central arterial blood pressure by real-time analysis of the oscillometric signals of the pressure.

Within the measuring device (10) of the present invention, the analytic device (40) can calculate the value of systolic blood pressure, diastolic blood pressure, average pressure, and heart rate. In an embodiment, the recording and saving device (30) can record and save the oscillometric waveform of the pressure in the cuff, which includes the signal of dynamic oscillometric waveform (recorded during decrease period of pressure in the cuff) and signal of static oscillometric waveform (recorded when the pressure in the cuff decreased to certain degree), wherein the static oscillometric waveform is the so-called pulse volume recording.

The present invention further provides a method of estimating the central arterial blood pressure by measuring the signal of pulse oscillation of the brachium artery by cuff, which includes:
(1) detecting the oscillometric waveform in the cuff;
(2) adjusting the oscillometric waveform by the average blood pressure and diastolic blood pressure measured by the cuff to calculate (I) systolic blood pressure of pulse volume recording, (II) last phase systolic blood pressure of pulse volume recording, (III) the value of the area below the waveform during systole and the area below the waveform during diastole dividing the area below the waveform during diastole, and (IV) the pressure of reflected wave hiding beneath the waveform of pressure; and
(3) bringing factors (I)~(IV) to a formula, a regression formula, to measure the measured central arterial blood pressure, and serve the measured central arterial blood pressure as dependent variable; the factor (I)~(IV) in Step (2) as independent variable, and then to solve the formula.

As shown in FIG. 2, the method of the present invention apply the formula, with known parameters, systolic pressure of pulse volume recording, last phase systolic blood pressure of pulse volume recording, the value of the area below the waveform during systole and the area below the waveform during diastole dividing the area below the waveform during diastole, the pressure of reflected wave hiding beneath the waveform of pressure, the heart rate, and the pressure of the reflected pressure, to calculate the central arterial systolic blood pressure.

In an embodiment of the present invention, the measurement of the oscillometric waveform of the pressure in the cuff includes the process of pressure decreasing in the cuff, the moment of the pressure in the cuff decreasing to a certain degree (for example, 60 mmHg) for a certain period, and the oscillometric signal recorded during the process of the pressure re-increasing in the cuff.

EXAMPLES

Example 1

Figure 1:
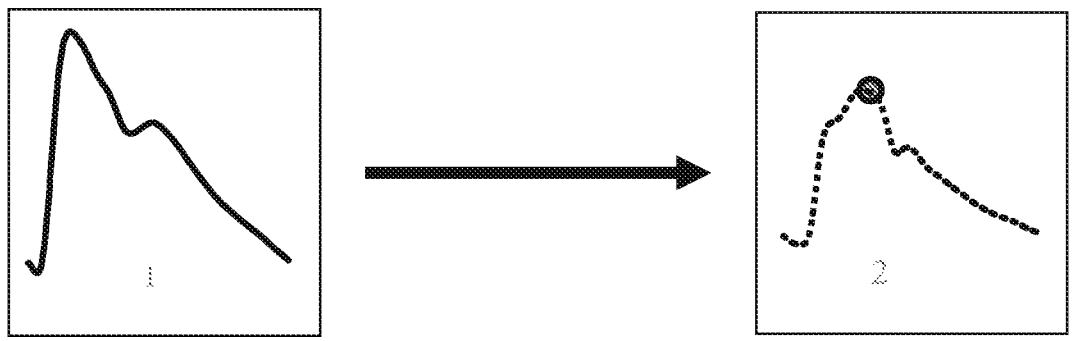
FIG. 1A shows the concept of the present invention, wherein 1 is the oscillometric waveform of the brachium artery pulse, 2 is the waveform of the central arterial blood pressure, and the black circle is the systolic central arterial blood pressure.
FIG. 1B depicts the image of the present invention, wherein 10 is the device of the present invention, 20 is the controlling device of the pressure change in the cuff, 30 is the recording and saving device of oscillometric signals of the pressure in the cuff, and 40 is the analytic device of analyzing the oscillometric signals of the pressure in the cuff.
Figure 1:
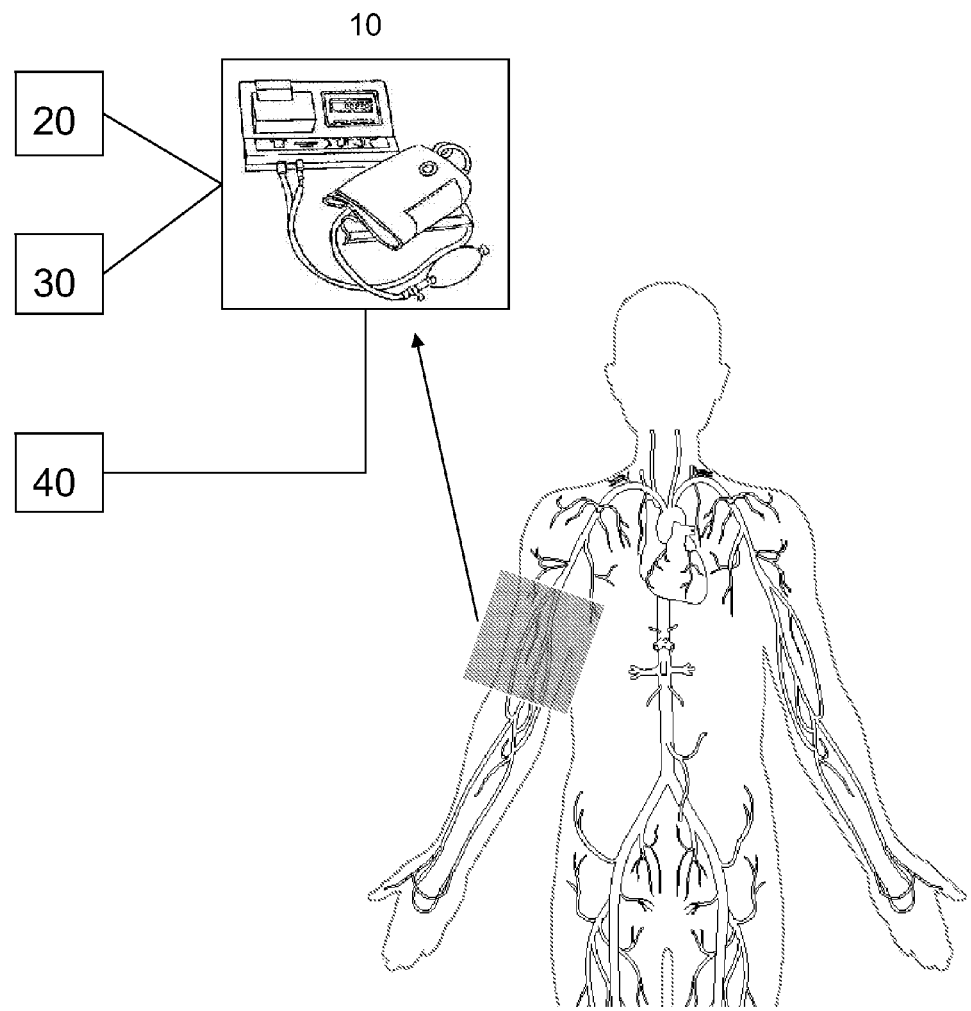
Figure 2:
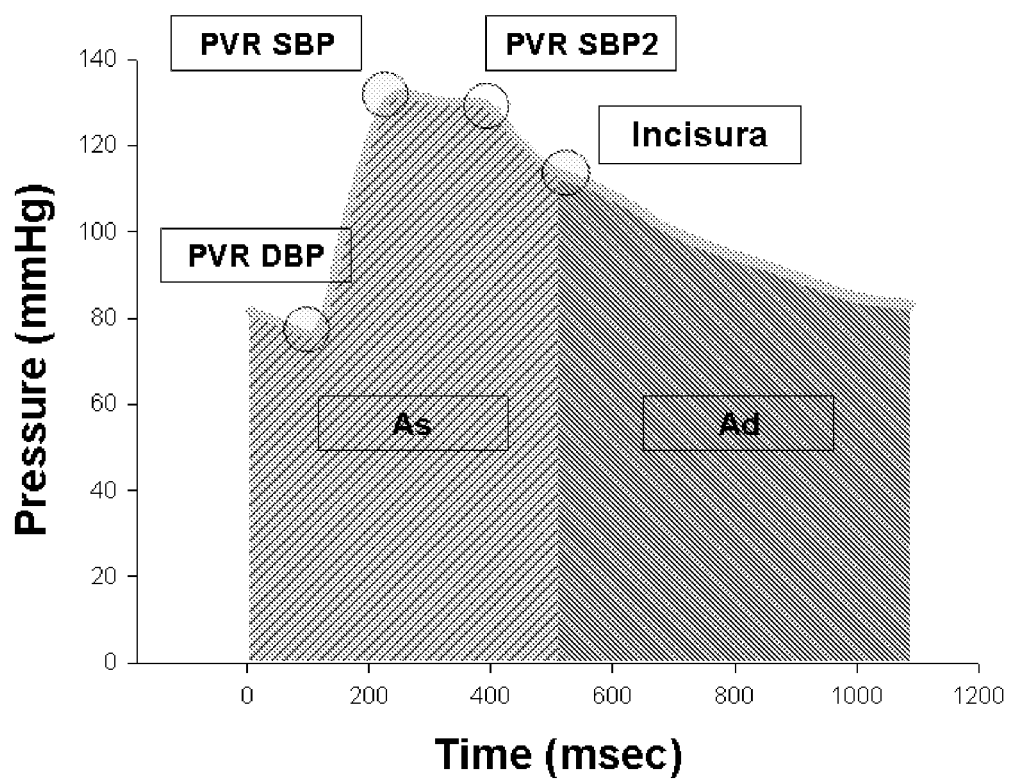
FIG. 2 depicts the diagram of the brachium artery pulse volume recording of the method of the present invention, wherein PVR SBP is abbreviated form "pulse volume recording of systolic blood pressure"; PVR DBP is abbreviated form "pulse volume recording of diastolic blood pressure"; the incisura is the last phase systolic blood pressure of pulse volume recording; As is the area below the waveform during systole; Ad is the area below the waveform during diastole; and PVR SBP2 is the reflected wave pressure pulse recorded during pulse volume recording.
Figure 3:
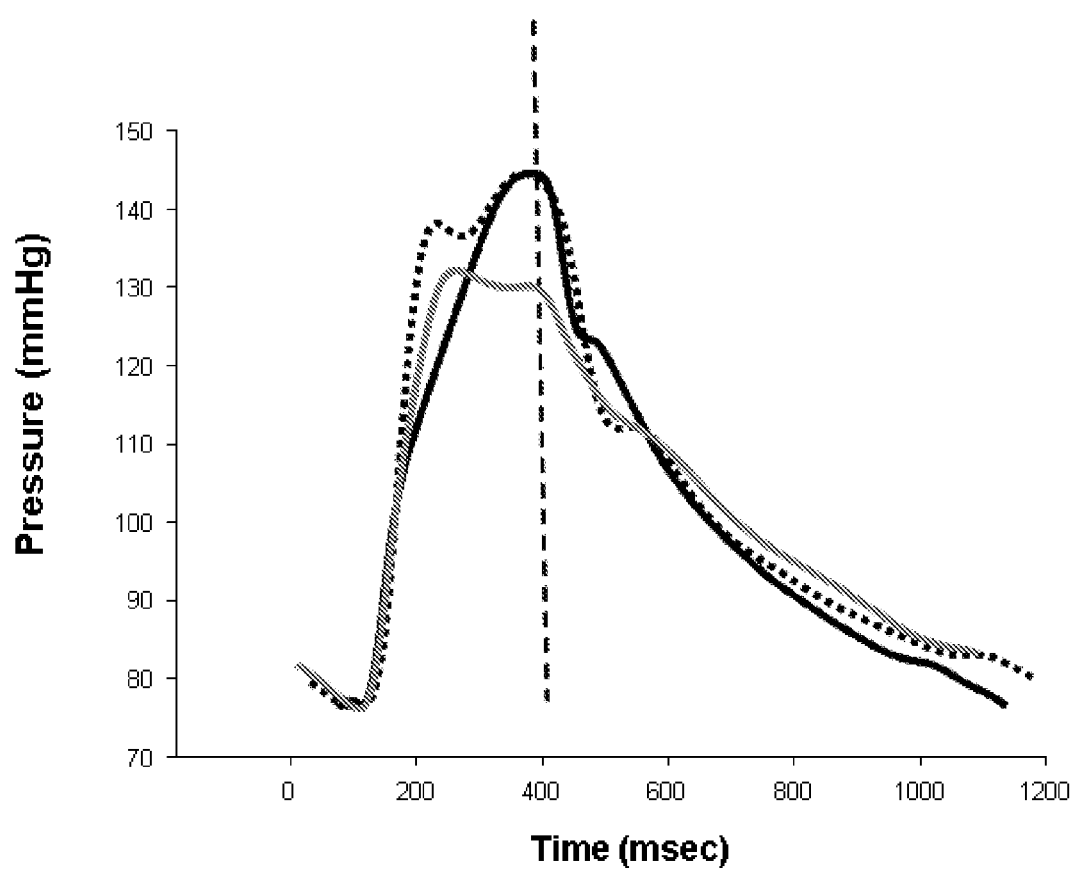
FIG. 3 shows several different waveforms recorded in Example 1, wherein the dotted is the waveform of the brachium arterial systolic blood pressure; the black is the waveform of the ascending aortic systolic blood pressure; the gray is the waveform of pulse volume recording; and the vertical dotted line refers to the time point of reflected wave pressure.

Invasive Procedures 50 experimenters participated in this experiment. After completion of routine catheterization, a micromanometer-tipped catheter (model SPC-320, Millar Instruments Inc) placed within the lumen of a standard 7F Judkins coronary artery catheter was advanced in the ascending aorta from right radial artery. The central aortic pressure waveform was recorded simultaneously with the noninvasive pulse volume recording. The recording was repeated during hemodynamic transient: at the peak response of intravenous bolus of 200 ug nitroglycerin. Once the signals had obtained by micromanometer in ascending aorta were recorded, the catheter was pulled back, leaving the micromanometer tip in the right brachial artery beneath the pressure cuff for the brachial pulse volume recording. Again, the invasive brachial pressure waveforms and the noninvasive brachial pulse volume traces were recorded simultaneously. The invasive central aortic and brachial pressure signals were digitized at a rate of 500 Hz on an IBM-compatible personal computer and saved for off-line analysis. The pulse volume recording was performed using the same device and technique as described in the first year project. The result was shown in FIG. 3.

Data Analysis

The digitized signals were analyzed using custom software written in our laboratory. Two to 10 consecutive beats of the carotid arterial pressure waves, brachial pulse volume traces, and radial artery pressure waves were signal averaged. Premature beats and beats immediately after premature beats were excluded. The signal-averaged carotid and radial arterial pressure wave and brachial pulse volume recording were calibrated by matching the mean and diastolic blood pressures of brachial artery pressure measured by the automated oscillometric sphygmomanometer incorporated in the device. The peak and lowest value of pressure waves and brachial pulse volume traces were recorded as systolic blood pressure and diastolic blood pressure, respectively. Waveforms were phase aligned, and point-by-point differences and regressions were used to compare waves. Overall agreement between the brachial pulse volume recording, carotid, radial, and reconstructed aortic pressure waveforms were quantified by the sum of squares of these differences normalized to the number of data points. Comparisons were examined by linear regression analysis with calibrated carotid artery pressures or reconstructed central aortic pressures as the dependent variables. In addition, frequency domain analysis for waveforms were performed by Fourier transformed and difference between waveforms less than 20 Hz were compared. The discrete Fourier transform of the time-averaged waves was evaluated by a commercial software package (routine fft.m in Matlab, version 4.2, The MathWorks) to yield the modulus and phase angle up to the 20th harmonic. The power spectral densities of the two spectra were calculated as the squared modulus values for each harmonic. The spectrum of the brachial PVR and radial tonometry were normalized to that of the carotid pressure wave by equating the total power of the two spectra. The transfer function between different pressure waves was then evaluated by both the differences and ratios of the moduli and by differences of the phase angles. The result was shown in FIG. 3.

Prediction of Central Systolic Blood Pressure by Statistical Regression Equation of Systolic Blood Pressure Estimated from Calibrated Brachial Pulse Volume Recording Multiple linear regression analysis was performed for prediction of central aortic systolic blood pressure. This model will include primarily the systolic blood pressure estimated from brachial pulse volume recording, age, gender, body weight, height, waist circumference, hip girdle length, and disease history. Central aortic systolic blood pressure was used as dependent variable. Unvaried correlation analyses with central aortic systolic blood pressure were performed and variables above with p value less than 0.15 were selected as independent variables in the model. Model R2, partial R2, and β coefficient, were calculated for prediction of central aortic systolic blood pressure.

Figure 4:
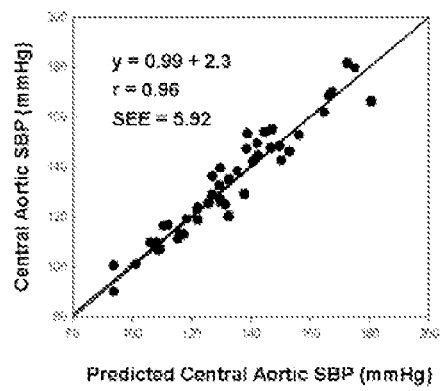
FIG. 4 shows the result of Example 1.
Figure 4:
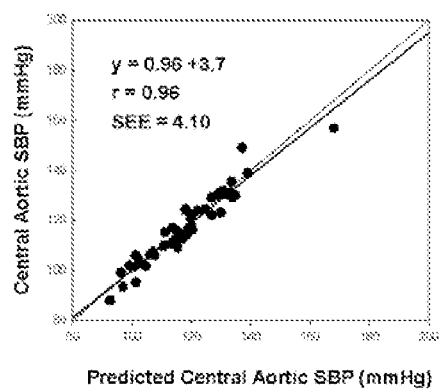
Figure 4:
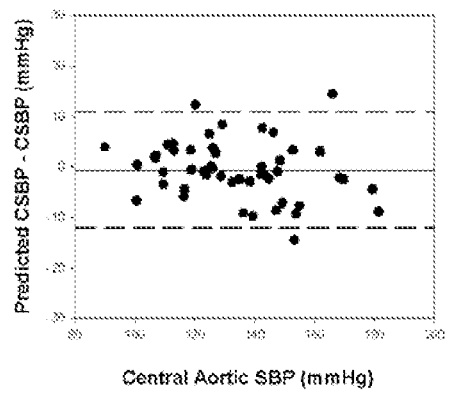
Figure 4:
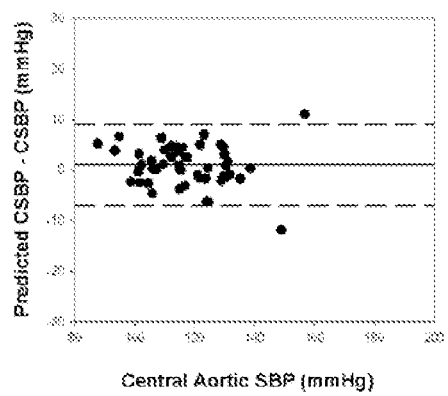

Statistical analysis was performed using SPSS 13.0. For assessment of parameters derived from tonometry and pulse volume recording, a paired student t test was performed. Simple linear regression was used to determine the relationship between measured parameters. A value of $p=0.05$ was considered statistically significant. The result was shown in FIG. 4, wherein the prediction of central aortic systolic blood pressure is similar to the real one before the nitroglycerine treatment, and so did the prediction after 3 minutes of the nitroglycerine treatment.

Example 2

Figure 5:
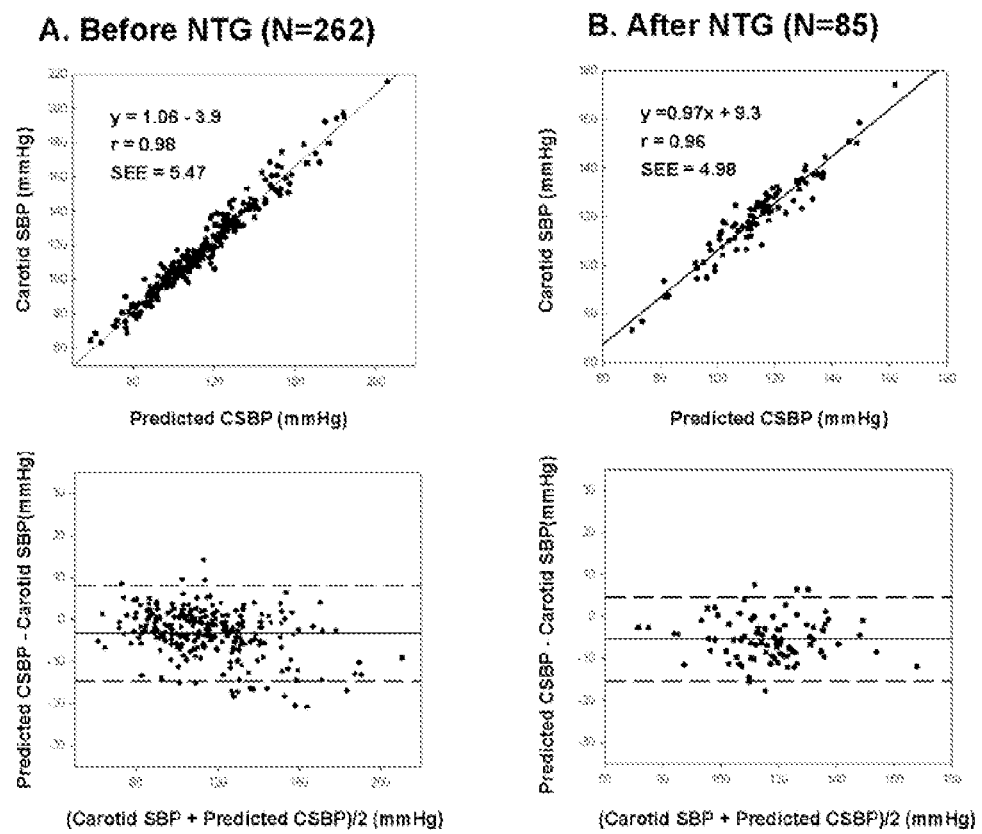
FIG. 5 shows the result of Example 2.

FIG. 5 showed the result of the application of the present invention on 262 experimenters, who have taken the carotid arterial pressure measurement simultaneously. The carotid arterial pressure, which was obtained from the recording of pressure waveform by non-invasive recorder via the adjustment of the brachium arterial average pressure and the brachium arterial diastolic blood pressure measured by electronic manometer, could represent the central arterial pressure. The comparison of the 262 experimenters in basic situation was shown in FIG. 5A, wherein 85 were treated by nitroglycerine and were tested again after 3 minutes (the result was shown in FIG. 5B). According to the result, the device and the method of the present invention both measured the central arterial systolic blood pressure accurately under the basic and nitroglycerine-treated situation.

What is claimed is:

1. A measuring device for estimating a central arterial blood pressure at a remote site, which includes:
   (1) means for controlling a pressure change in a cuff during a process of pressurization, decompression or maintenance at a specific pressure value;
   (2) means for recording and saving oscillometric signals of a pressure in the cuff; and
   (3) means for analyzing the oscillometric signals of the pressure in the cuff, and for estimating the central arterial blood pressure by real-time analysis of the oscillometric signals of the pressure by performing an equation of estimating the central arterial blood pressure by a known regression formula on the basis of factors (I) systolic blood pressure of pulse volume recording, (II) last phase systolic blood pressure of pulse volume recording, (III) a value of an area below a waveform during systole and an area below a waveform during diastole dividing the area below the waveform during diastole, and (IV) a pressure of reflected wave hiding beneath a waveform of pressure, in which all factors (I) to (IV) are identified or measured from waveforms of the pulse volume recording.

2. The measuring device of claim 1, wherein the means for analyzing the oscillometric signals of the pressure in the cuff calculate the brachium arterial blood pressure value.

3. The measuring device of claim 2, wherein the brachium arterial blood pressure value includes systolic blood pressure, average blood pressure, diastolic blood pressure, and heart rate.

4. The measuring device of claim 1, wherein the central artery is a carotid artery or the ascending aorta.

5. The measuring device of claim 1, wherein the oscillometric signals of the pressure, include the signals in a dynamic oscillometric waveform recorded during a decrease period of the pressure in the cuff and in a static oscillometric waveform recorded when the pressure in the cuff is decreased to a certain degree.

* * * * *